US005733600A

United States Patent [19]
McCabe

[11] Patent Number: 5,733,600
[45] Date of Patent: Mar. 31, 1998

[54] METHOD AND APPARATUS FOR PREPARING SAMPLE CARTRIDGES FOR A PARTICLE ACCELERATION DEVICE

[75] Inventor: Dennis E. McCabe, Middleton, Wis.

[73] Assignee: PowderJect Vaccines, Inc., Madison, Wis.

[21] Appl. No.: 747,870

[22] Filed: Nov. 13, 1996

[51] Int. Cl.$^6$ .......... B05D 7/22

[52] U.S. Cl. .......... 427/183; 427/181; 427/230; 427/231; 427/2.1; 427/2.11

[58] Field of Search .......... 427/181, 183, 427/231, 232, 233, 335, 378, 240, 2.1, 2.11; 118/55

[56] References Cited

U.S. PATENT DOCUMENTS

| | | | |
|---|---|---|---|
| 4,298,634 | 11/1981 | Phelps | 427/183 |
| 4,597,995 | 7/1986 | Snow et al. | 427/231 |
| 4,822,692 | 4/1989 | Koehler | 428/547 |
| 4,945,050 | 7/1990 | Sanford et al. . | |
| 4,987,013 | 1/1991 | Atkins et al. | 427/233 |
| 5,015,580 | 5/1991 | Christou et al. . | |
| 5,120,657 | 6/1992 | McCabe et al. . | |
| 5,149,655 | 9/1992 | McCabe et al. . | |
| 5,204,253 | 4/1993 | Sanford et al. . | |
| 5,372,761 | 12/1994 | Anderson, Sr. | 264/36 |
| 5,405,779 | 4/1995 | McCabe et al. . | |
| 5,584,807 | 12/1996 | McCabe | 604/71 |

OTHER PUBLICATIONS

Klein, T.M., et al., "Particle Gun Technology: A Novel Method for the Introduction of DNA into Living Cells," Abstract for Post 28 in *Biotechnology in Plant Science: Relevance to Agriculture in the Eighties*, International Symposium, Ithaca NY (1985).

Klein, T.M., et al., "High Velocity Microprojectiles for Delivering Nucleic Acids into Living Cells," *Nature*, 327:70–73 (1987).

Klein, T.M., et al., "Stable Genetic Transformation of Intact *Nicotiana* Cells by the Particle Bombardment Process," *Proc. Natl. Acad. Sci. USA*, 85:8502–8505 (1988).

McCabe, D.E., et al., "Stable Transformation of Soybean (*Glycine max*) by Particle Acceleration," *Bio/Technology*, 6:923–926 (1988).

Sanford, J.C., "The Biolistic Process," *TIBECH*, 6:299–302 (1988).

Sanford, J.C., et al., "Delivery of Substances into Cells and Tissues Using a Particle Bombardment Process," *Particulate Science and Techn.*, 5:27–38 (1987).

*Primary Examiner*—Shrive Beck
*Assistant Examiner*—Michael Barr
*Attorney, Agent, or Firm*—Robins & Associates

[57] ABSTRACT

Particles coated with biological substances are deposited onto the concave inner surface of a length of tubing by a process which includes preparing a uniform suspension of coated particles and introducing the particles into the tubing while rotating horizontally. Then the speed of rotation is increased to drive the particles out of suspension and against the inner surface. After particle separation, the rotational speed is decreased and a gas is passed through the tubing to blow out the separated liquid. Next both the speed of rotation and the gas flow rate are increased to dry the particles that have been deposited against the inner surface of the tubing. An apparatus for performing the method also is disclosed.

16 Claims, 2 Drawing Sheets

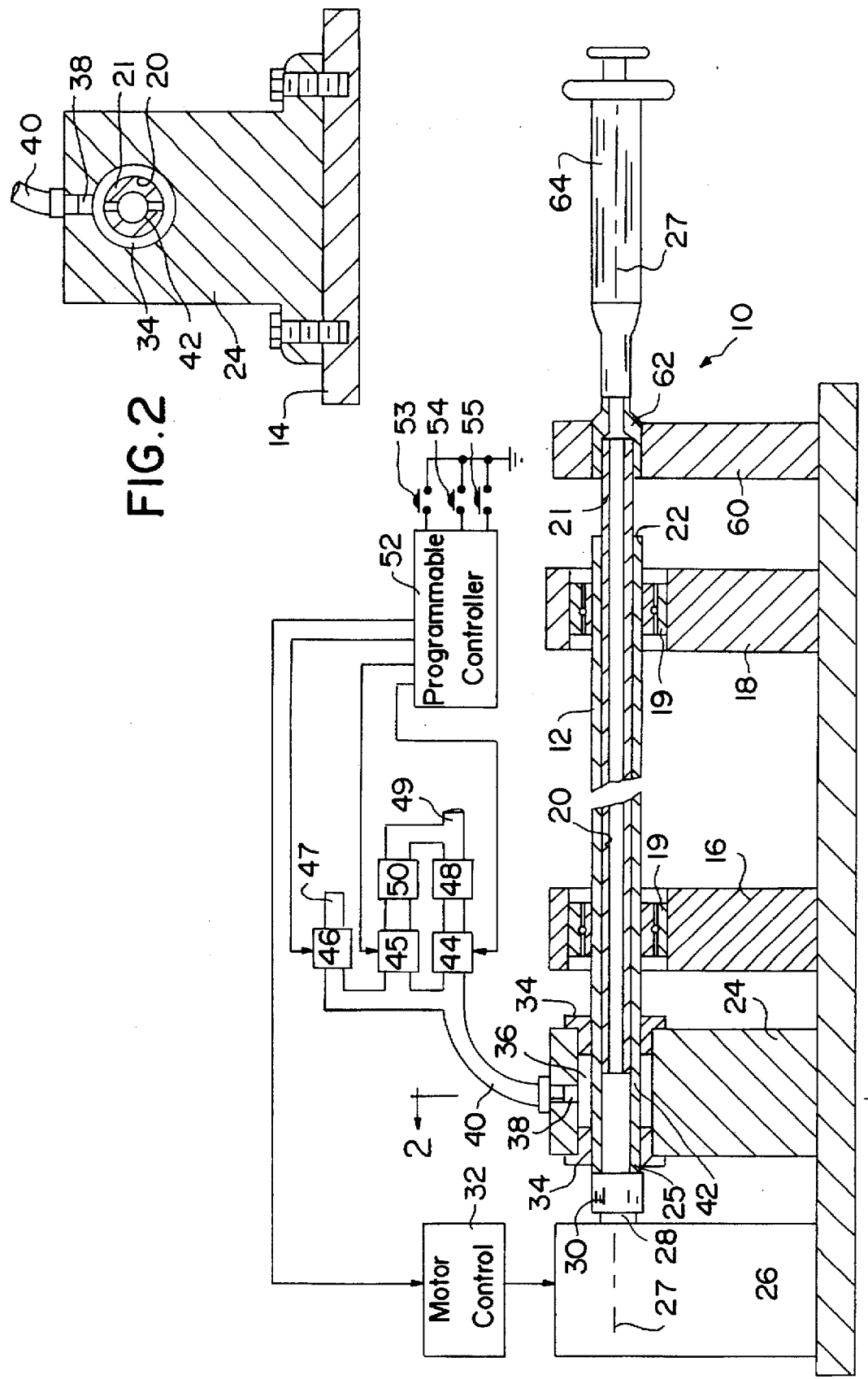

```
┌─────────┐
│  START  │
└────┬────┘
     ▼
┌──────────────────────┐
│ COAT PARTICLES WITH  │
│ BIOLOGICAL MATERIAL  │
└──────────┬───────────┘
           ▼
┌──────────────────────────┐
│ ROTATE TUBING AT 50-200 RPM │
└──────────┬───────────────┘
           ▼
┌──────────────────┐
│ OPEN VENT VALVE  │
└────────┬─────────┘
         ▼
┌──────────────────────┐
│ INTRODUCE PARTICLE   │
│ SOLUTION INTO TUBING │
└──────────┬───────────┘
           ▼
┌──────────────────┐
│ CLOSE VENT VALVE │
└────────┬─────────┘
         ▼
┌──────────────────────────────┐
│ ROTATE AT 2000 RPM FOR 15 SECONDS │
└──────────────┬───────────────┘
               ▼
┌────────────────────────────────────────┐
│ ROTATE AT 1000 RPM FOR 55 SECONDS      │
│ AND OPEN GAS VALVE FOR 2.5-3.5 ml/min  │
└──────────────────┬─────────────────────┘
                   ▼
┌────────────────────────────────────────┐
│ ROTATE AT 5000 RPM FOR 2 MINUTES       │
│ AND OPEN GAS VALVE FOR 500-800 ml/min  │
└──────────────────┬─────────────────────┘
                   ▼
               ┌───────┐
               │  END  │
               └───────┘
```

METHOD AND APPARATUS FOR PREPARING SAMPLE CARTRIDGES FOR A PARTICLE ACCELERATION DEVICE

FIELD OF THE INVENTION

The present invention relates to the field of delivering particles coated with biological substances into cells and more particularly to a method and apparatus for preparing samples for delivery.

BACKGROUND OF THE INVENTION

In the past decade, particle-mediated acceleration of material, particularly genetic material, into living cells and tissues has emerged as an important tool of plant and animal biotechnology. Transient expression and germ line integration of introduced DNA has been demonstrated in microorganisms, plants, and animals.

As the fundamentals of the technology have been worked out, attention has increasingly shifted toward development of devices that offer a technician the ability to perform a series of particle-mediated gene transfers sequentially in rapid succession. Such a device would be particularly advantageous for use in mass immunization of humans or domesticated animals with genetic vaccines.

To that end, an instrument was developed for accelerating the particles coated with biological substances using a compressed gas. The biological sample is deposited upon the surface of small, dense particles of a material, such as gold or platinum, which may be spherically shaped. The coated particles are themselves then coated onto the interior curved surface of a rigid tube. The coated tube, or cartridge, is loaded into the instrument and aligned with a barrel. When a valve opened, compressed gas flows through the coated tube and the barrel blowing off, the carrier particles which accelerated toward a biological target.

Thus it is advantageous to uniformly coat the interior of the tube with particles that carry the biological sample and be able to produce the same uniform coating on numerous tubes.

SUMMARY OF THE INVENTION

A general object of the present invention is to provide a method and an apparatus for forming a large number of particle cartridges for use in a gas driven particle acceleration instrument.

A further object is to provide such a method and an apparatus which uniformly coats the cartridges with the particles to be accelerated.

These and other objects are satisfied by a method for depositing particles in a length of tubing which comprises the steps of preparing in an evaporable liquid a uniformly dispersed suspension of particles, distributing the uniformly dispersed particle suspension on a concave inner surface of a length of tubing, removing most of the evaporable liquid from the tubing but not particles which settle on the inner surface, and then drying the deposited particles.

Before being deposited, the particles are coated at a suitable density with a biological substance for delivery into a biological target. The particles are of sufficiently small size in relation to the size of the biological target which they are intended to transform and sufficiently dense to readily retain momentum to penetrate the biological target.

The apparatus for depositing particles in a length of tubing according to this method comprises a tubing roller having an horizontal axis of rotation and a tubing bore concentric with the axis of rotation. The tubing bore has first and second ends and is sized for removable insertion of the tubing therein. The tubing roller is rotatably supported in a generally horizontal orientation and a rotator is operably connected to spin the tubing roller. A particle suspension delivery mechanism is removably attachable to introduce the particles into one end of the tubing and a gas delivery coupling is connected to the tubing bore to introduce a drying gas through the tubing.

The prepared suspended particles are introduced by this apparatus into a piece of tubing placed into the tubing bore. During the introduction, the tubing rotates so that the solution carrying the particles does not pool at the lower region of the tubing interior. After the suspension of particles has been inserted, the rotational speed is increased to separate the particles from the carrier liquid, thereby centrifugally driving the particles against the curved interior surface of the tubing. Then the speed is decreased to a level which prevents recombination of the liquid and particles. A compressed gas, such as air or nitrogen, is passed through the tubing to drive out the separated liquid carrier. Once that exhaustion has occurred, the speed is increased and a higher gas flow rate dries the particles that continue to be centrifugally forced against the curved interior surface of the tubing. When the deposition is complete, the coated tubing is removed from the apparatus and cut into individual cartridges.

It is an advantage of the present invention that a large number of substantially identical sample cartridges can be prepared in a single effort. The present centrifugal method produces tubes that are very uniform, as compared to previous techniques, and lends itself to automation of the process.

Other objects, advantages and features of the present invention will become apparent upon consideration of the following specification read in conjunction with the accompanying drawings.

BRIEF DESCRIPTION OF THE DRAWINGS

FIG. 1 is a cut away view of a preferred embodiment of the present invention;

FIG. 2 is a cross sectional view along line 2—2 in FIG. 1; and

FIG. 3 is a flowchart of steps in the process to deposit coated particles in a cartridge for a particle acceleration instrument.

DETAILED DESCRIPTION OF THE INVENTION

The present invention provides a reproducible method for forming a large number of sample cartridges for use in a gas-driven particle acceleration instrument. Small dense particles are reversibly coated onto a concave inner surface of the sample cartridges. The particles are themselves reversibly coated with biological substances such as genetic material or protein. During particle acceleration and delivery, a gas stream passing over the deposited particles releases the particles from the sample cartridge and carries them into a target cell, tissue, or organism.

For repeatability of delivery, it is important that the number of particles delivered from each sample cartridge be ascertainable and relatively constant, at least within a statistically acceptable range, such as ±10% for example, of an experimentally determined mean number. Also important is that particle distribution among the sample cartridges be substantially constant, to maximize sample-to-sample reproducibility.

Deposition Apparatus

With reference to FIG. 1, a suitable apparatus 10 for performing the present deposition procedure includes a tubing roller 12 rotatably mounted to a base 14 in a generally horizontal orientation by two or more mounts 16 and 18. The base 14 can be of any size and shape, and should be at least as long as the particle-filled tubing that is intended to be coated. The base 14 can include leveling means and a spirit level to facilitate the horizontal positioning of the tubing roller. The mounts 16 and 18 are attached to, or formed as part of, the base 14 and have bearing 19 which rotatably engage the tubing roller 12 to direct proper rotation about the axis of rotation with minimal friction and precession. The mounts 16 and 18 and the tubing roller 12 are preferably rotatably engaged with each other at or near the ends of the tubing roller. Depending upon the length of the tubing roller 12 additional mounts may be provided between mounts 16 and 18 as needed to prevent vibration at the relatively high rotational speed used during the coating process.

The tubing roller 12 can be formed of any solid, durable material such as metal, plastic, wood or the like. In the illustrated preferred configuration of the tubing roller 12 is cylindrical. The tubing roller 12 has sufficient length along the axis of rotation to receive and secure substantially the entire length of the tubing to be coated.

The mounted tubing roller 12 has an axis of rotation and a tubing bore 20 which is coaxial with the axis of rotation. The tubing bore 20 is positioned so that a length of tubing 21 received therein shares the same axis of rotation as the tubing roller 12 and extends into the tubing roller from an opening 22 at a first end of the tubing roller. The tubing bore 20 is sized in length, width and depth to accommodate the tubing 21 and preferably is generally cylindrical. To facilitate insertion of the tubing 21 into the tubing bore 20, the opening 22 of the tubing bore is wider than the bore 20 itself and preferably flares outward from the bore 20. The opposite second end 25 of the tubing bore 20 is capped. The tubing bore 20 is mounted concentric with the rotational axis 27 of the apparatus 10.

The capped second end of the tubing roller passes through a gas delivery mount 24 and is operably connected to a rotator 26 that directs rotation of the tubing roller 12 about the axis of rotation. The rotator 26 can be powered in any way for example, electrical or mechanical energy powering direct or indirect rotation of the tubing roller 12, but must provide sufficient power to rotate the tubing roller 12 about the axis of rotation at various constant rates between 50 and 6000 revolutions per minute (RPM) for at least two minutes. The rotator 26 can be connected to any portion of the tubing roller 12, as long as axial rotation is not constrained. Preferably a shaft 28 of the rotator 26 is attached by a fitting 30 directly to the capped second end of the tubing roller 12. A suitable rotator 26 that can attach directly to the shaft 28 is an electrically actuated gear motor, such as a Barnant Mixer Series 20 motor, which can be remotely controlled using an associated variable speed motor control 32. The rotator 26 need not be attached to the base 14, but is preferably attached thereto for increased stability.

As noted previously a portion of the tubing roller 12 passes through a gas delivery mount 24 as shown in FIGS. 1 and 2. Specifically, the tubing roller 12 extends through an aperture in the gas delivery mount 24 and is sealingly supported at the openings of the aperture by a pair of bushings 34 formed of a durable, low friction material. The bushings seal the aperture openings and define an interior chamber 36 in the aperture. Alternatively sealed bearings may be utilized in place of bushings 34 as long as the sealed bearings can operate at the rotational speeds of the present process described subsequently. A passage 38 is provided in the gas delivery mount 24 through which to introduce gas from conduit 40 into the interior chamber 36. A transverse aperture 42 extends through the tubing roller 12 to provide communication between the interior chamber 36 and the tubing bore 20 allowing the gas from conduit 40 to enter the tubing bore. The interior chamber 36 extends completely around the tubing roller 12 so that the communication between the conduit 40 and the interior chamber is continuous as the tubing roller is spun on axis 27 by the rotator 26. Thus the gas delivery mount 24 enables continuous uninterrupted delivery of a drying gas from an external source at a suitably controlled flow rate into the second end of the bore 20.

The gas conduit 40 is connected to three electrically operated valves 44, 45 and 46. The inlet side of the first valve 44 is coupled for a first flow regulator 48 which allows gas to flow therethrough at a fixed rate between 2.5–3.5 milliliter per minute. Similarly the inlet side of the second valve 45 is coupled for a second flow regulator 50 which allows gas to flow therethrough at another fixed rate between 500–800 milliliters per minute. The two flow regulators are connected via a supply hose 49 to a source of a compressed drying gas, such as air or nitrogen. The electrically operated vent valve 46 connects the gas conduit 40 to an atmospheric vent port 47.

The operation of the components of the deposition apparatus 10 may be controlled manually, but preferably is governed by a commercially available programmable controller 52. The programmable controller 52 has outputs connected to the speed control 32 and the three valves 44–46. Inputs of the programmable controller 52 are connected to three push button switches 53, 54 and 55 by which a technician designates operating modes of load, spin and stop, respectively.

Particle Preparation

The process by which biological material is deposited on the inner surface of the tubing is depicted in the flowchart of FIG. 3. The first step in this process involves coating the delivery particles with the biological material.

Methods for coating the small, dense particles with a biological substance for use in the novel tubing deposition process are known. Any such method can be used to prepare the coated particles, however a preferred method for coating DNA onto gold particles for use in the particle-depositing method will be described. One of ordinary skill will appreciate from the following description the importance of determining, with an acceptable tolerance, the amount of biological substance per particle and the number of particles per sample cartridge. The acceptable tolerance levels should be about ±30%, preferably about ±20% and most preferably about ±10% of the desired amount.

Gold particles are preferred for coating. References herein to "beads" or "particles" are intended to include, without limitation, both spherical and amorphous particles of appropriate size and density. DNA is a preferred biological substance for coating onto particles. However, other substances including, but not limited to, RNA and proteinaceous materials can also be coated onto the particles. The subsequent description and examples refer to the use of gold particles coated with DNA, although the invention is not intended to be so limited. Conditions for depositing other biological substances or for using non-gold particles can vary from the method stated in ways that are understood in the art.

A desired amount of the gold particles is placed in a centrifuge tube. The amount of gold used can be roughly determined by multiplying the desired number of particles per delivery by the number of sample cartridges being prepared, i.e. the number of cartridges produced from one piece of tubing 21. A suitable amount of particles per delivery is typically on the order of 0.25–0.50 milligrams gold per delivery, although acceptable amounts can be higher or lower. By routine experimentation, one can ascertain limits on particle delivery amounts below which the transfer is acceptably high (by any ascertainable measure, such as gene expression level or biological response to treatment) while the trauma to target tissues is minimal. Minimal trauma in an animal target tissue is evidenced by only a slight reddening of the target area.

A small quantity (100–300 microliter) of 0.1M spermidine is added to the centrifuge tube and a suspension of single particles is formed by sonicating the tube contents for a sufficient length of time, generally for a few seconds.

An appropriate volume of DNA, suspended in a buffer that does not affect its integrity or stability, is added to the particle/spermidine suspension to achieve an acceptable DNA loading rate. The DNA, spermidine, and gold particles are mixed by vortexing. The DNA loading rate is the average density of DNA per particle, expressed for a bulk population (e.g., micrograms of DNA per milligram of particles). Preferred effective DNA loading rates on gold particles range from 0.1 to 5.0 micrograms of DNA per milligram of gold. Exceeding 10.0 micrograms of DNA per milligram of gold is not preferred as it can lead to clumping of gold particles. However, as little as 0.001 micrograms of DNA per milligram of gold is adequate to achieve significant expression from some expression vectors.

It is noted that, to obtain the most uniform coating results, the volume of DNA should not exceed the volume of spermidine, but smaller volumes may be used. Accordingly, it may be necessary to adjust either the concentration of plasmid DNA or the volume of spermidine added initially to the gold particles.

Calcium chloride ($CaCl_2$) then is added to the mixture while gently vortexing. A sufficient amount of calcium chloride is added to result in precipitation of DNA-coated gold particles. If 2.5M calcium chloride is added, a suitable volume is equal to the volume of spermidine added earlier. The mixture is allowed to precipitate at room temperature for at least five or ten minutes. At DNA loading rates of 1.0 micrograms of DNA per milligram of gold or higher, precipitation should be apparent immediately after calcium chloride is added.

After precipitation, the tube is centrifuged briefly (10–15 seconds) to pellet the coated gold particles. The supernatant is removed and discarded and the pellet is washed several times with ethanol until virtually all of the water has been removed from the coated particle preparation. Between each ethanol wash, the preparation is spun and the supernatant discarded. The coated particles of the final pellet, containing known amounts of both DNA and gold, are resuspended in an evaporable liquid, preferably 100% ethanol, optionally containing an appropriate amount of an additive that provides a slight temporary adhesive effect desired for joining the coated particles to the sample, cartridge. A suitable adhesive is polyvinyl pyrrolidone (PVP). The amount of adhesive required in the evaporable liquid depends upon the gas pressure to which the sample cartridges will be exposed during subsequent particle acceleration and also upon the type of tubing used. For gas pressures in the range of 100 to 150 psi, no adhesive is required. Between 150 and 300 psi, PVP at 0.001 to 0.01 milligrams per milliliter is appropriate. PVP at 0.01 to 0.05 milligrams per milliliter is suitable at pressures between 300 and 500 psi or higher. At pressures of 500–800 psi, 0.3 milligrams per milliliter of PVP is a suitable amount.

Some care should be taken in determining the total volume in which to resuspend the coated particles. The volume depends upon the desired amount of biological substance per delivery, the actual DNA loading rate, the desired particle density in the final sample cartridge, and the internal volume per length of tubing. One of ordinary skill will also recognize that the preferred amount of DNA per delivery and particles per delivery will vary with the nature of the target, the density at which the particles are coated, and the desired outcome of the transfer (e.g. transient expression or stable integration). Therefore, each of the stated variables, including the concentration at which the particles are loaded into the tubing, should be experimentally optimized.

After settling upon a desired particle loading rate, desired particle density and the volume capacity per unit length of tubing, one can readily determine the total volume of the evaporable liquid in which to resuspend the coated particles. A suitable sample cartridge length has been found to be about a 12.7 millimeter length of tubing having in internal capacity of between about 0.6 and 1.0milliliter per 17.78 centimeter length. For tubing with that internal capacity, simple calculation demonstrates that if 0.5 milligrams of gold are desired in a 12.7 millimeter sample cartridge, the particles are prepared at a concentration of 7.0 milligrams of gold per milliliter. Likewise, for a 0.25 milligram sample in a 12.7 millimeter cartridge, a 3.5 milligram per milliliter concentration is appropriate. Concentrations that achieve other particle densities are calculated in the same way.

To achieve complete transfer of the coated particles into the evaporable liquid, it is recommended that the pellet be transferred to the storage tube in several partial transfer steps. For example, the coated particles can be resuspended in a small volume (500 microliters) of the liquid with optional adhesive, vortexed, briefly sonicated (2–3 seconds) and transferred to a clean tube. It is recommended that the tube be formed of a material to which the biological substances do not stick, such as polypropylene culture tube. These small volume transfers can be repeated until all the coated particles have been transferred to the tube. If desired, the tubes containing suspended coated particles can be sealed with Parafilm and stored for several months at −20° C. When the coated particles have been completely transferred, preparation of the sample cartridges can begin. Previously stored tubes should be warmed to room temperature before unsealing for use in the particle-depositing method.

Tube Coating Process

To prepare sample cartridges, suitable tubing having a concave arcuate inner surface is filled with a uniform suspension of the coated particles in the evaporable liquid. It is preferred that the tubing be transparent or translucent so that the particles coated onto the inner concave surface can be visually observed. All tubing used should be inert to reaction with the selected drying gas (preferably nitrogen) and should be sufficiently durable to retain mechanical stability throughout the gene delivery process. Tefzel® tubing (⅛" outer diameter ×3/32" inner diameter) has been found to be suitable. This size tubing has an internal capacity of about 0.8 milliliter per 17.78 centimeter of length.

Referring to FIG. 1, with the deposition apparatus turned off, the tubing 21 to be coated is inserted through opening 22 into the horizontal tubing roller 12 where the tubing snugly engages the surface of bore 20 so that the two components will rotate together. A portion of the tubing 21 is left projecting from the opening 22 with the length of that portion being measured so that the tubing will not be inserted so far into the tubing roller 12 as to block the gas flow aperture 42 near the remote end of the bore 20. A removable support 60 then is secured to the base 14 with a slip bearing 62 of the support receiving the exposed end of the tubing 21. The slip bearing 62 engages the outer diametric surface of the tubing 21 in a manner that provides a fluid-tight seal there between while allowing the tubing to rotate within the slip bearing which is held stationary in the support 60.

The coated-particle suspension in a storage container is vortexed and sonicated to achieve uniform distribution of the coated particles. A charge of previously coated particles in suspension is drawn into a barrel syringe 64, which has an resilient coupling that is adapted to fit onto an exposed end of the slip bearing 62 as shown in FIG. 1.

With the filled syringe 64 attached to slip bearing 62, the technician presses the "load" switch 53. In response, the programmable controller 52 opens the vent valve 50 and commands the speed control 32 to activate the rotator 26 to turn the tubing roller 12 and the tubing 21 at 50–200 RPM. The plunger of the syringe 64 then is pushed by the technician to force the coated particles into the tubing 21. By turning the tube while emptying the syringe, the particles are prevented from setting to the lower region of the bore in the horizontally extending tubing 21. Venting the remote end of the tubing 21 to the ambient atmosphere via vent valve 50 prevents pressure build-up in the tube during introduction of the coated particles.

After the biologically coated particles have been transferred to the tubing 21, the syringe 64 is removed from the slip bearing 62. Next the technician presses the "spin" switch 54. The programmable controller 52 responds to this action by closing the vent valve 50 and commanding speed control 32 to increase the rotational speed of the tubing roller 12 and thus the tubing 21 to about 1700 to 2300 RPM, with 2000 RPM being preferred. The tubes spin at this speed for at least approximately 15 seconds which centrifugally forces the particles out of suspension and against the concave arcuate inner surface of the tubing 21 forming a uniform layer.

After the layer forms, the settled particles are dried by first expelling the supernatant from the tubing. This is readily achieved by introducing a drying gas, such as air or nitrogen gas, into one end of the tubing. At this point, the programmable controller 52 automatically decreases the rotation to between about 700 to 1300 RPM, with 1000 RPM preferred. At the same time, the first gas valve 44 is opened by the programmable controller 52, which causes compressed gas from supply hose 49 to flow into the second end of the tubing roller 12 at a rate of about 2.5–3.5 milliliters per minute as determined by the setting of the first regulator 48. This gas flow blows the separated supernatant from the tubing 21 through the slip bearing 62. Operation under these conditions continues for about 55 seconds, which is sufficient to expel the supernatant at which point the first gas valve 44 is closed.

Finally, the settled particles are dried by removing the residual evaporable liquid from the tubing 21. To accomplish this, the programmable controller 52 increases the speed of rotation to between about 4000 and 6000 RPM, with 5000 RPM being preferred, which further centrifugally separates the particles from the carrier liquid. At that time, the second valve 45 is opened by the programmable controller 52, which causes gas to flow into the second end of the tubing roller 12 at about 500–800 milliliters per minute as determined by the setting of the second regulator 48. This increased gas flow evaporates the carrier leaving the biologically coated particles adhering in a uniform layer to the concave arcuate inner surface of the tubing 21. The final drying step lasts for approximately two minutes or until the particles are completely dry. After the drying cycle is finished, the to programmable controller 52 closes the second gas valve 45 and instructs the speed control 32 to stop the rotator 26. The coated tubing 21 then may be removed from the deposition apparatus 10.

Before the tubing is cut into suitable lengths for the sample cartridges as described above, it is necessary to remove any end portions of the tubing in which particle distribution is uneven. The distribution of particles in the tubing can be tested operationally in the gas driven particle acceleration apparatus under actual delivery conditions. The following test conditions are suitable, although other tests for determining and comparing the particle delivery profile of prepared sample cartridges can readily be devised.

Test cartridges of desired length are removed from opposite ends of the tubing. The particles from each test cartridge are released from the concave inner surface under a gas pressure of 400 psi and are directed into minimal water (3%) agar in 60 millimeter petri dishes without surface condensation. From each plate, a slice approximately one centimeter long is cut through the center of the target agar and mounted onto a microscope slide. It is important to test slices of comparable thickness when samples are compared. The slices are analyzed for particle depth and particle number under a microscope. The particles can be readily observed using a microscope having a 10 X eyepiece equipped with a micrometer. At the top surface of the agar, the particles are most dense, with density decreasing with increasing depth into the agar slice. Areas of high, medium, and low particle density are noted in each slice. The eyepiece micrometer is aligned to zero at a depth approximately equal to the deepest penetration of the particles. The micrometer value at the agar surface is the particle depth. Typical particle depths after delivery into minimal water agar at 400 psi are about 100–120 micrometers when 0.95 micron amorphous gold particles are used and about 260–300 micrometers for 1–3 micron gold spherical particles or beads.

If particle depth and density are similar, then cartridges derived from tubing section between the ends are acceptable for use. However, should the two ends differ markedly from each other or standard coating parameters, additional pairs of opposite end samples should be tested until both ends yield comparable acceptable results. When comparable results are obtained from both ends, the remaining length of tubing is cut into pieces of suitable length using a scalpel and a ruler or other type of cutting device. The sample cartridges thus prepared can be stored at 4° C. with desiccant in a Parafilm-sealed and labelled vial for up to two months at 4° C.

The foregoing description is directed primarily to preferred embodiments of the invention. Although some attention was given to various alternatives within the scope of the invention, it is anticipated that skilled artisans will likely realize additional alternatives that are now apparent from the disclosure of those embodiments. Accordingly, the scope of the invention should be determined from the following claims and not limited by the above disclosure.

I claim:

1. A method for depositing particles in a length of tubing having a longitudinal axis and a curved interior surface, the method comprising the steps of:
    (a) preparing a uniformly dispersed suspension of particles coated with a biological substance in an evaporable liquid;
    (b) rotating the tubing about its longitudinal axis at a first speed;
    (c) introducing the particle suspension into the tubing while rotating said tubing at the first speed;
    (d) rotating the tubing to centrifugally separate the particles from the evaporable liquid and distribute the particles on the interior surface of the tubing; and
    (e) passing a gas through the tubing as the tubing rotates to dry the particles distributed on the interior surface.

2. The method as recited in claim 1, wherein step (c) comprises:
    loading a syringe with the suspension;
    coupling the syringe to an end of the tubing; and
    transferring the suspension from the syringe into the tubing.

3. The method as recited in claim 1, wherein steps (b) through (e) are performed with the longitudinal axis of the tubing oriented horizontally.

4. The method as recited in claim 1, wherein the tube is rotated at a speed of about 50 to 200 revolutions per minute in step (b).

5. The method as recited in claim 1, wherein the tubing is rotated in step (d) at a second speed which is greater than the first speed.

6. The method as recited in claim 5 wherein the second speed is between about 1700 and 2300 revolutions per minute.

7. The method as recited in claim 5, wherein the tubing is rotated in step (e) at a speed which is greater than the first speed.

8. The method as recited in claim 5, wherein step (e) comprises:
    passing a gas at a first flow rate through the tubing as the tubing rotates to remove the evaporable liquid therefrom; and
    passing a gas at a second flow rate through the tubing as the tubing rotates to dry the particles distributed on the interior surface of said tubing, wherein the second flow rate is greater than the first flow rate.

9. The method as recited in claim 8 wherein the step of passing a gas at a first flow rate occurs while the tubing is rotating at a third speed which is less that the second speed.

10. The method as recited in claim 9 wherein the third speed is between about 700 and 1300 revolutions per minute.

11. The method as recited in claim 9 wherein the step of passing a gas at a second flow rate occurs while the tubing is rotating at a fourth speed which is greater than the third speed.

12. The method recited in claim 11 wherein the fourth speed is between about 4000 and 6000 revolutions per minute.

13. The method as recited in claim 1, wherein the step of passing a gas through the tubing comprises:
    passing a gas at a first flow rate through the tubing as the tubing rotates to remove the evaporable liquid therefrom; and
    passing a gas at a second flow rate through the tubing as the tubing rotates to dry the particles distributed on the interior surface of said tubing, wherein the second flow rate is greater than the first flow rate.

14. The method recited in claim 13 wherein the first flow rate is between about 2.5 and 3.5 milliliters per minute.

15. The method recited in claim 13 wherein the second flow rate is between about 500 and 800 milliliters per minute.

16. The method as recited in claim 1 wherein the gas is selected from the group consisting of air and nitrogen.

* * * * *